(12) United States Patent
Yoneyama

(10) Patent No.: US 10,484,581 B2
(45) Date of Patent: Nov. 19, 2019

(54) IMAGE PICKUP APPARATUS FOR ENDOSCOPE

(71) Applicant: OLYMPUS CORPORATION, Tokyo (JP)

(72) Inventor: Jumpei Yoneyama, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 60 days.

(21) Appl. No.: 15/817,941

(22) Filed: Nov. 20, 2017

(65) Prior Publication Data
US 2018/0077325 A1 Mar. 15, 2018

Related U.S. Application Data

(63) Continuation of application No. PCT/JP2015/067850, filed on Jun. 22, 2015.

(51) Int. Cl.
A01B 1/04 (2006.01)
H04N 5/225 (2006.01)
A61B 1/04 (2006.01)
A61B 1/00 (2006.01)
G02B 23/24 (2006.01)
A61B 1/05 (2006.01)

(52) U.S. Cl.
CPC ......... H04N 5/2253 (2013.01); A61B 1/0011 (2013.01); A61B 1/00045 (2013.01); A61B 1/04 (2013.01); A61B 1/051 (2013.01); G02B 23/2484 (2013.01); H04N 2005/2255 (2013.01)

(58) Field of Classification Search
CPC ........................................................ A61B 1/00

USPC .................................................... 348/65–76
See application file for complete search history.

(56) References Cited

U.S. PATENT DOCUMENTS 5,217,001 A * 6/1993 Nakao ............... A61B 1/00135
24/DIG. 50
6,447,447 B1 * 9/2002 Mitsumori ......... A61B 1/00188
600/129
2015/0014805 A1 1/2015 Yamada

FOREIGN PATENT DOCUMENTS

| JP | H08-115893 A | 5/1996 |
| JP | H10-289916 A | 10/1998 |
| JP | 2013-219468 A | 10/2013 |
| JP | 2015-029774 A | 2/2015 |
| WO | WO 2013/150813 A1 | 10/2013 |

OTHER PUBLICATIONS

International Search Report dated Sep. 29, 2015 issued in PCT/JP2015/067850.

* cited by examiner

Primary Examiner — Anand S Rao
(74) Attorney, Agent, or Firm — Scully, Scott, Murphy & Presser, P.C.

(57) ABSTRACT

An image pickup apparatus for an endoscope includes: an image pickup device including a row of external electrodes provided on an end portion of a light receiving surface; and a wiring board including end portion electrodes ultrasonically bonded to the external electrodes, in which a plurality of grooves are formed in a back face of the image pickup device, and the plurality of grooves are inclined relative to a vibration direction of ultrasonic vibration during the ultrasonic bonding.

8 Claims, 12 Drawing Sheets

IMAGE PICKUP APPARATUS FOR ENDOSCOPE

CROSS REFERENCE TO RELATED APPLICATION

This application is a continuation application of PCT/JP2015/067850 filed on Jun. 22, 2015, the entire contents of which are incorporated herein by this reference.

BACKGROUND OF INVENTION

1. Field of the Invention

The present invention relates to an image pickup apparatus for an endoscope, the image pickup apparatus including an image pickup device including external electrodes on a light receiving surface and a wiring board including end portion electrodes ultrasonically bonded to the external electrode.

2. Description of the Related Art

Electronic endoscopes each including an image pickup apparatus including an image pickup device such as a CMOS light receiving element in a distal end portion of an insertion portion have been in widespread use. A flexible elongated insertion portion of a medical endoscope, in which an image pickup apparatus is incorporated in a distal end portion, is inserted into a body cavity of a subject such as a patient to perform, e.g., observation of a site to be examined.

The image pickup device transmits/receives an electric signal via external electrodes bonded to end portion electrodes of a wiring board. Reliability of the bonding between the external electrodes of the image pickup device and the end portion electrodes of the wiring board is one of major factors in reliability of the endoscope. Also, the image pickup device may be deteriorated by high-temperature processing such as solder bonding.

Thus, for the bonding between the external electrodes and the end portion electrodes, ultrasonic bonding enabling strong bonding at a low temperature is used. For ensuring ultrasonic bonding, it is necessary to secure an image pickup device held by an anvil of an ultrasonic bonding apparatus so as to prevent vibration of the image pickup device by ultrasonic vibration. Thus, in some cases, the anvil is added with any of various anti-slip mechanisms such as a vacuum mechanism and side clamps.

Japanese Patent Application Laid-Open Publication No. 10-289916 describes a semiconductor apparatus including a heat sink plate ultrasonically bonded to a die pad of a lead frame. A group of anti-slip grooves is formed in a surface of an anvil on which the die pad is mounted, for raising a friction coefficient.

SUMMARY OF THE INVENTION

An image pickup apparatus for an endoscope according to an embodiment of the present invention is an image pickup apparatus for an endoscope, the image pickup apparatus including: an image pickup device including a row of external electrodes provided on an end portion of a light receiving surface; and a wiring board including end portion electrodes ultrasonically bonded to the external electrodes, wherein a plurality of grooves are formed in a back face of the image pickup device, the back face facing the light receiving surface, and the plurality of grooves are inclined relative to a vibration direction of ultrasonic vibration during ultrasonic bonding.

DETAILED DESCRIPTION OF THE PREFERRED EMBODIMENT

Embodiment

Figure 1:
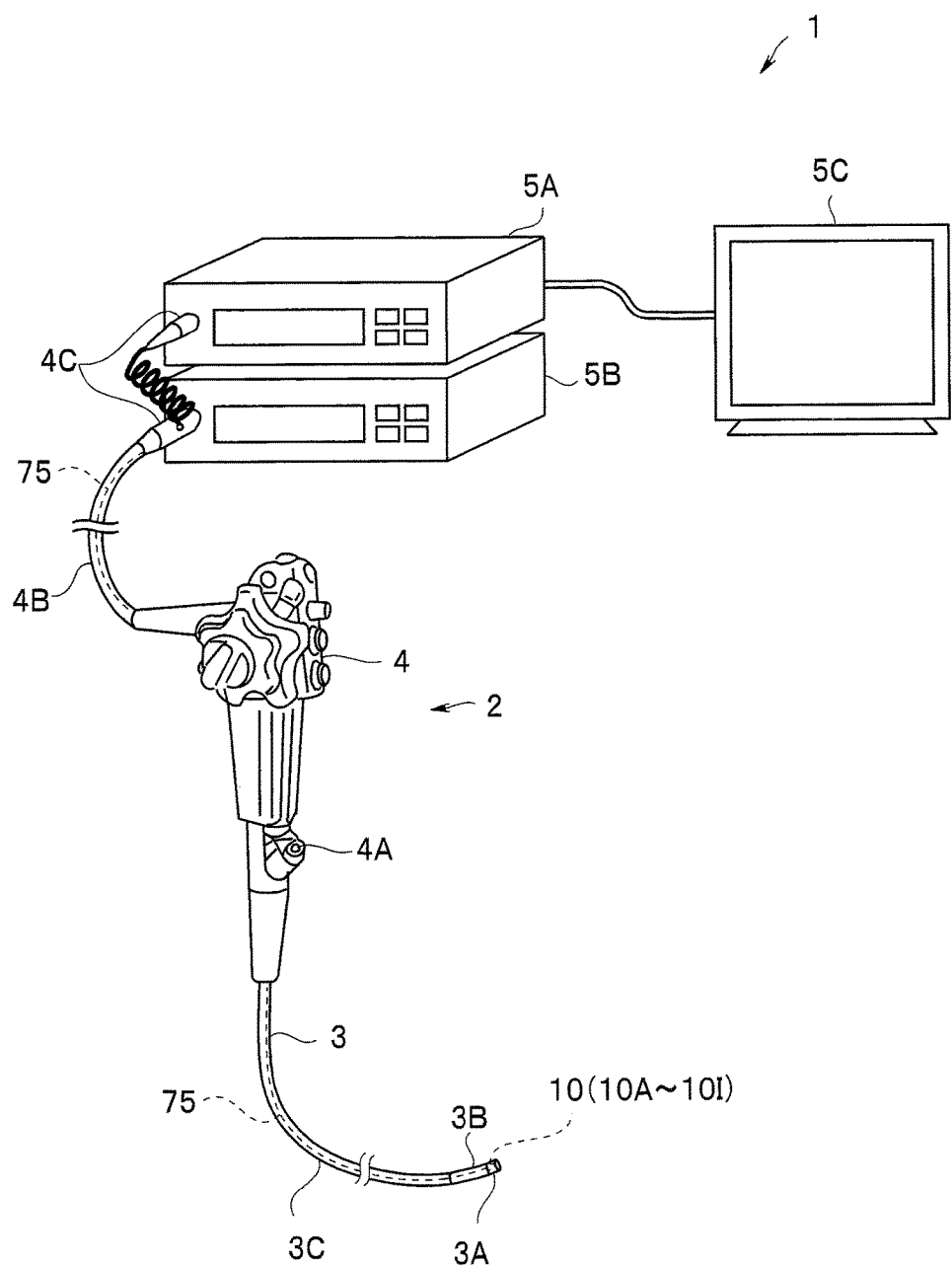
FIG. 1 is a diagram of an outer appearance of an endoscope system including an image pickup apparatus according to an embodiment.
Figure 2:
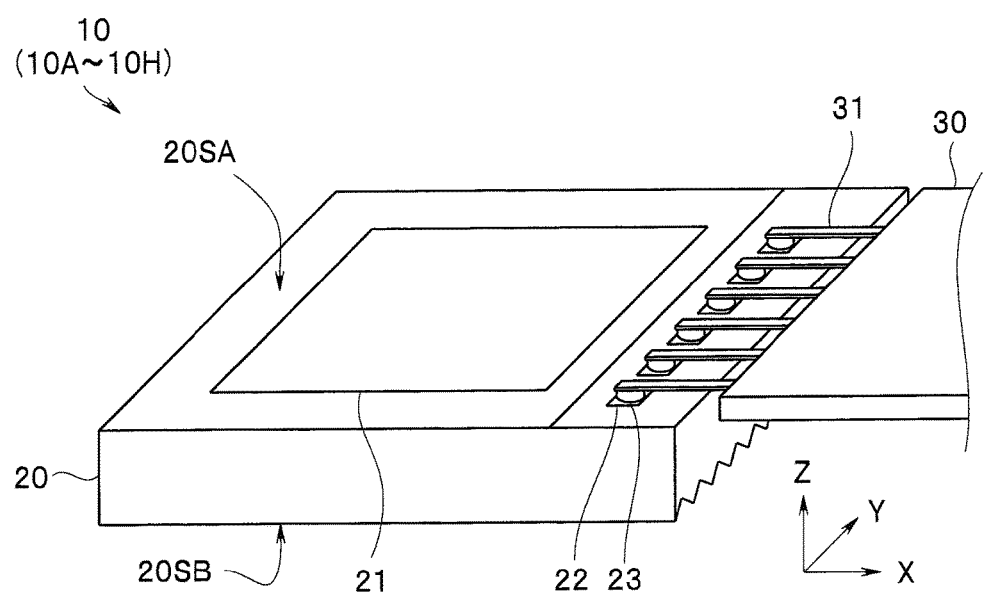
FIG. 2 is a perspective view of the image pickup apparatus according to the embodiment.
Figure 3:
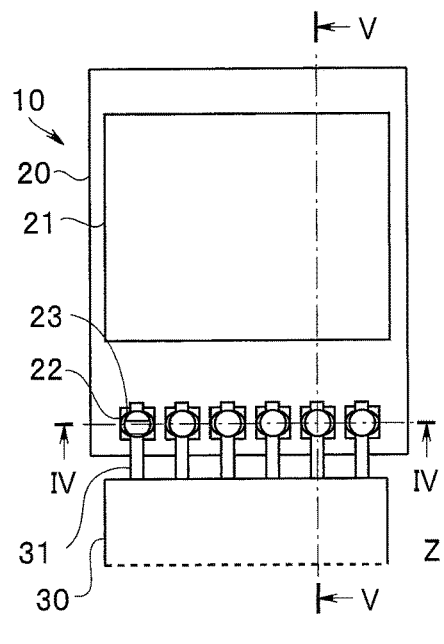
FIG. 3 is a top view of the image pickup apparatus according to the embodiment.

An endoscope system 1 including an endoscope 2 including an image pickup apparatus 10 for an endoscope (hereinafter also referred to as "image pickup apparatus") according to an embodiment of the present invention will be described with reference to FIG. 1.

Here, it should be noted that the drawings are schematic ones and, e.g., a relationship between a thickness and a width of each part and ratios in thickness among the respective parts are different from actual ones, and parts that are different in dimensional relationship and ratio depending on the drawings may be included in the drawings. Also, projections and recesses of surfaces are illustrated in enlargement.

As illustrated in FIG. 1, the endoscope system 1 includes the endoscope 2, a processor 5A, a light source apparatus 5B and a monitor 5C. An elongated insertion portion 3 of the endoscope 2 is inserted into a body cavity of a subject, allowing the endoscope 2 to pick up an image of the inside of the body of the subject and output an image pickup signal.

An operation portion 4 provided with various types of buttons for operating the endoscope 2 is disposed on the proximal end side of the insertion portion 3 of the endoscope 2. The operation portion 4 includes a treatment instrument insertion opening 4A of a channel from which a treatment instrument such as biological forceps, an electric scalpel or an examination probe is inserted into a body cavity of a subject.

The insertion portion 3 includes a distal end portion 3A in which an image pickup apparatus 10 is disposed, a bendable bending portion 3B provided so as to be continuous with the proximal end side of the distal end portion 3A, and a flexible tube portion 3C provided so as to be continuous with the proximal end side of the bending portion 3B. The bending portion 3B is bent by operation of the operation portion 4.

A signal cable 75 connected to the image pickup apparatus 10 in the distal end portion 3A is inserted through a universal cord 4B disposed on the proximal end portion side of the operation portion 4.

The universal cord 4B is connected to the processor 5A and the light source apparatus 5B via the connector 4C. The processor 5A controls the entire endoscope system 1, and performs signal processing of an image pickup signal outputted by the image pickup apparatus 10 and outputs the resulting signal as an image signal. The monitor 5C displays the image signal outputted by the processor 5A.

The light source apparatus 5B includes, for example, a white LED. Light emitted by the light source apparatus 5B is guided to the distal end portion 3A via a light guide (not illustrated) inserted through the universal cord 4B and the insertion portion 3 and illuminates a subject.

As illustrated in FIGS. 2 to 6, the image pickup apparatus 10 for an endoscope includes an image pickup device 20 and a wiring board 30. On a light receiving surface 20SA of the image pickup device 20 having a rectangular shape in plan view, a light receiving section 21 and a plurality of external electrodes 22 electrically connected to the light receiving section 21 are formed. The image pickup device 20 includes a light receiving surface 20SA and a back face 20SB facing the light receiving surface 20SA. A row of the plurality of external electrodes 22 is provided in parallel to a short axis direction (Y direction) on an end portion of the light receiving surface 20SA of the image pickup device 20. Then, bumps 23 are disposed on the respective external electrodes 22.

The image pickup device 20 disposed in the distal end portion 3A of the endoscope 2 is extremely small, for example, 1.5 mm long (X-axis), 1 mm wide (Y-axis direction) and 0.3 mm thick (Z-axis direction) for invasion alleviation.

On the other hand, a plurality of flying leads 31 protrude from an end face of the wiring board 30. The flying leads 31, which are end portion electrodes, each include a conductor wiring resulting from selective removal of an insulating base of the wiring board 30. The flying leads 31 are called outer leads in a lead frame.

Distal end portions of the flying leads 31 are ultrasonically bonded to the external electrodes 22 via the bumps 23. Thus, the bumps 23 are crushed in a direction parallel to a vibration direction of ultrasonic vibration during the ultrasonic bonding, and numerous steaks (ultrasonic vibration marks) parallel to the vibration direction are formed in an upper surface of the distal end portion of each flying lead 31.

In the image pickup apparatus 10, the plurality of flying leads 31 and the plurality of external electrodes 22 are ultrasonically bonded to each other simultaneously. Then, the ultrasonic vibration direction is a direction in which a row of the bumps 23 is provided (Y direction: short-axis direction). Thus, the direction in which the bumps 23 are crushed and the direction of the ultrasonic vibration streaks are parallel to the direction of the row of the bumps 23.

Figure 4:
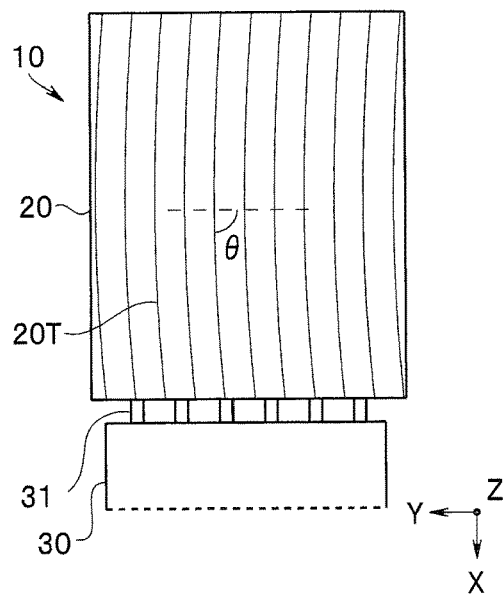
FIG. 4 is a bottom view of the image pickup apparatus according to the embodiment.
Figure 5:
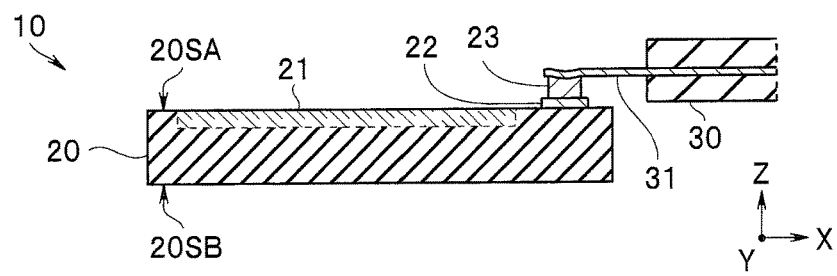
FIG. 5 is a cross-sectional view of the image pickup apparatus according to the embodiment along line V-V in FIG. 3.
Figure 6:
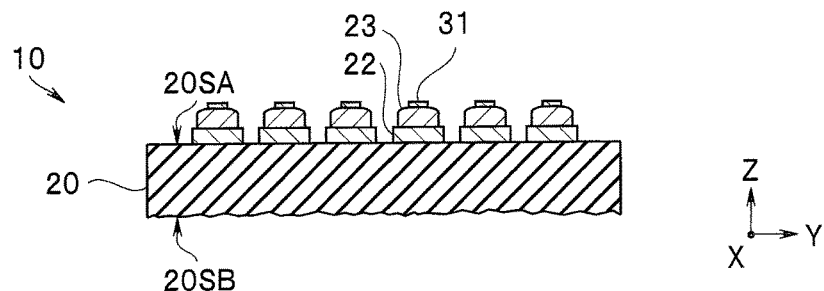
FIG. 6 is a cross-sectional view of the image pickup apparatus according to the embodiment along line IV-IV in FIG. 3.

Then, as illustrated in FIG. 4, a plurality of substantially-linear grooves 20T are formed in the back face 20SB of the image pickup device 20. As described later, the plurality of grooves 20T are saw marks (grinding marks) formed in a step of a wafer machining process for producing the image pickup device 20. The grooves formed in the wafer machining process can form a fine shape with high precision. A direction of the plurality of grooves 20T is inclined so as to be substantially orthogonal to the ultrasonic vibration direction (Y direction), that is, the direction of the row of the bumps 23.

Here, to be exact, the plurality of grooves 20T each have a circular arc shape, but are substantially orthogonal to the direction of the row of the bumps 23 in the entire back face 20SB. In other words, an inclination angle θ of the plurality of grooves 20T relative to the direction of the row of the bumps 23 (short axis direction: Y direction) is, for example, no less than 80 degrees and no more than 100 degrees.

In the image pickup device 20, the plurality of grooves 20T substantially orthogonal to the ultrasonic vibration direction (Y direction) are formed in the back face 20SB. Thus, even if ultrasonic vibration is applied to the image pickup device 20 mounted on an anvil 40, the image pickup device 20 is prevented from slipping on the anvil 40 because of the ultrasonic vibration V (see FIG. 14).

Thus, in the image pickup apparatus 10, reliability of the bonding between the bumps 23 of the image pickup device 20 and the flying leads 31 of the wiring board 30 is high.

Figure 7:
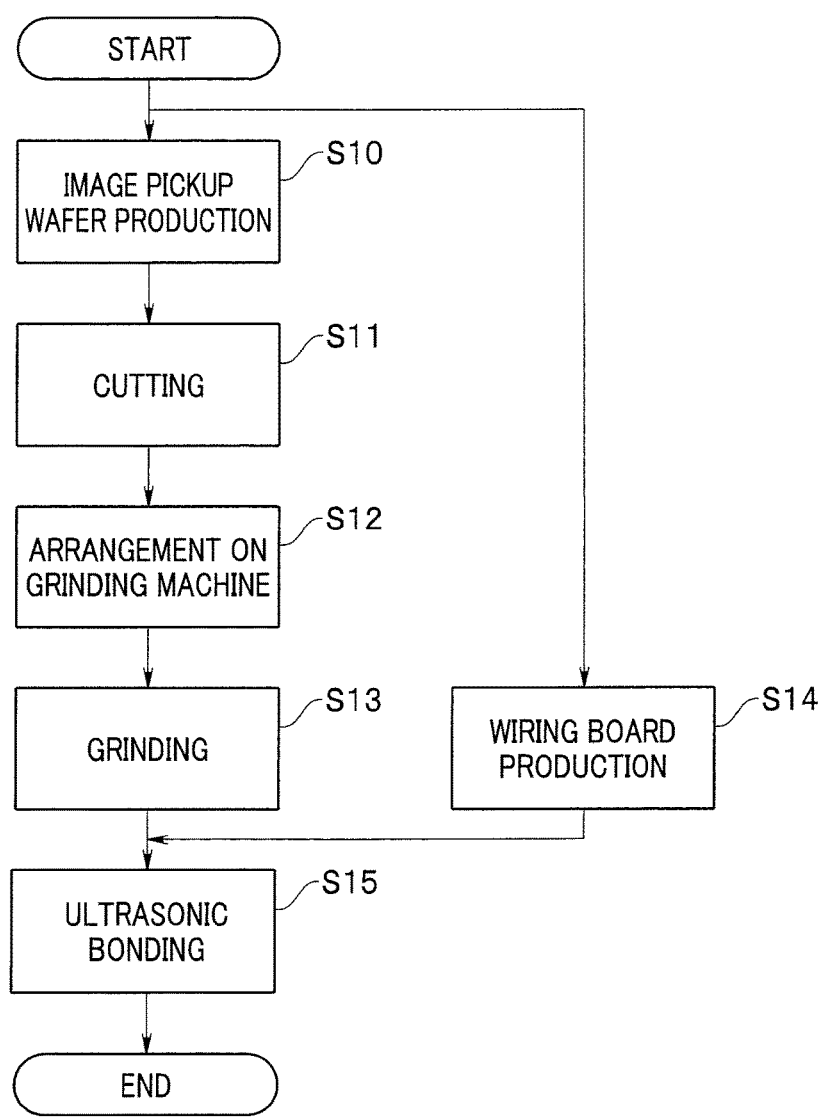
FIG. 7 is a flowchart for describing a method for manufacturing the image pickup apparatus according to the embodiment.

Next, a method for manufacturing the image pickup apparatus 10 will be described with reference to the flowchart illustrated in FIG. 7.

<Step S10: Image Pickup Wafer Production>

A plurality of light receiving sections 21 and a plurality of external electrodes 22 and a plurality of bumps 23 connected to each light receiving section 21 are formed on a first principal surface of a semiconductor substrate such as a silicon wafer using a known semiconductor process. Each light receiving section 21 is, e.g., a CCD (charge-coupled device) or a CMOS (complementary metal-oxide semiconductor). On the silicon wafer, not only the light receiving sections 21 but also semiconductor circuits such as signal processing circuits may be formed. Here, a thickness of a φ300 mm silicon wafer is, for example, 775 μm.

<Step S11: Cutting>

As a result of cutting of the silicon wafer, a plurality of image pickup devices 20 each including a light receiving section 21, etc., are produced. Each image pickup device 20 has a bottom outer dimension of, for example, 1 mm×1.5 mm, that is, a bottom area of 1.5 mm$^2$, and thus, is ultracompact. Here, the first principal surface, with the light receiving sections 21 formed, of the silicon wafer are cut into light receiving surfaces 20SA of the image pickup device 20.

<Step S12: Arrangement>

The image pickup devices 20 each have a thickness of, for example, 775 μm and thus are thick. For reduction in diameter of the insertion portions 3, the image pickup devices 20 are machined so as to have a thickness of, for example, no less than 20 μm and no more than 150 μm.

Figure 8:
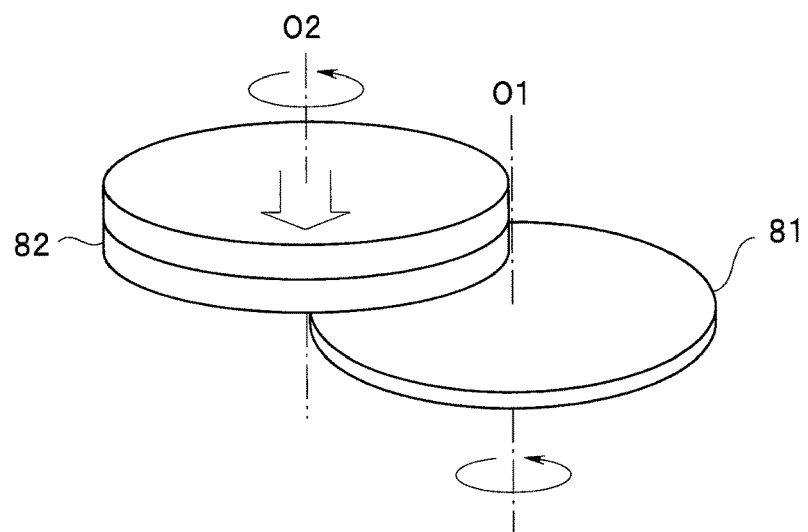
FIG. 8 is a schematic diagram for describing an in-feed-type grinding machine.

For reduction in thickness of the image pickup devices 20, grinding of a second principal surface (corresponding to back faces 20SB) is performed. FIG. 8 illustrates an example of a grinding machine 80. The in-feed-type grinding machine 80 includes a holder 81 on which an image pickup device 20, which is a workpiece, is to be mounted, and a grinder 82 configured to grind the image pickup device 20 mounted on the holder 81. On the grinder 82, for example, a plurality of grinding stones containing, for example, diamond abrasive grains are disposed. The image pickup device 20 is secured to the holder 81 via, e.g., a protection tape. The grinding machine 80 is of a centerless type in which a rotation axis O1 of the holder 81 and a rotation axis O1 of the grinder 82 are not aligned with each other.

Figure 9:
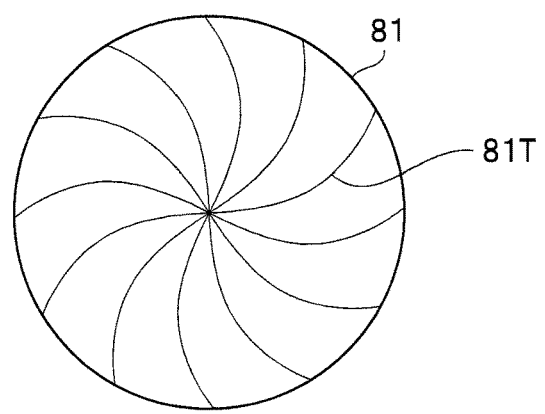
FIG. 9 is a diagram illustrating a direction of saw marks formed by the in-feed-type grinding machine.

Here, in the in-feed, centerless-type grinding machine 80, as illustrated in FIG. 9, radial saw marks (grooves 81T) are formed in a plurality of workpieces arranged on the holder 81.

Figure 10:
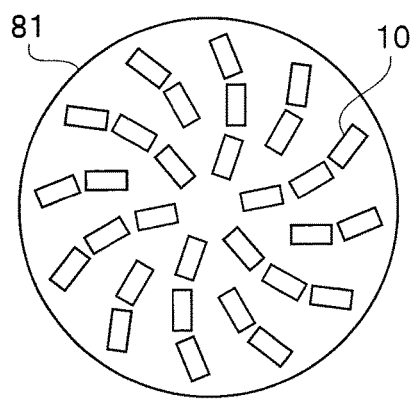
FIG. 10 is a diagram for describing the method for manufacturing the image pickup apparatus according to the embodiment.
Figure 11:
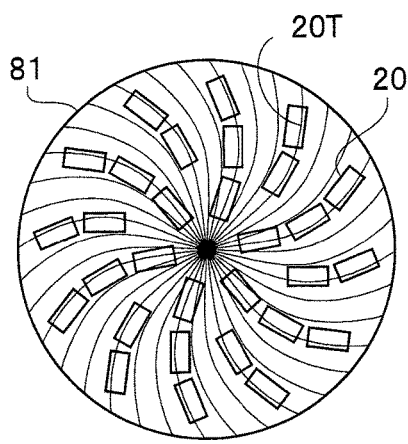
FIG. 11 is a diagram for describing arrangement of workpieces to be ground in the method for manufacturing the image pickup apparatus according to the embodiment.

In the method for manufacturing the image pickup apparatus 10 according to the present embodiment, as illustrated in FIG. 10, the plurality of image pickup devices 20 are arranged on the holder 81 in such a manner that a direction of a row of the bumps 23 is orthogonal to the direction in which the saw marks are formed. In other words, in a conventional image pickup apparatus manufacturing method, grinding is performed in the state of a semiconductor substrate (silicon wafer) including a plurality of image pickup devices. However, in the method for manufacturing the image pickup apparatus 10 according to the embodiment, before the back face grinding step, the silicon wafer is cut into the image pickup devices 20, the grinding is performed in the state of the image pickup devices 20. In other words, the plurality of image pickup devices 20 are re-arranged on the holder 81 in an arrangement that is different from an arrangement in the semiconductor substrate.

<Step S13: Grinding>

Back faces of the image pickup devices 20 are subjected to grinding so that a surface roughness Rz of each back face 20SB in a direction orthogonal to a direction of saw marks (grooves) (JIS B 060: ten-point average roughness, sampling length of 0.2 mm) becomes no less than 0.5 μm and no more than 10 μm. It is more preferable that the surface roughness Rz be no less than 1 μm and no more than 5 μm. Also, it is preferable that a surface roughness Rmax (JIS B 060: maximum height, sampling length of 0.2 mm) be no less than 1 μm and no more than 30 μm.

For invasion alleviation, an image pickup device for an endoscope includes, for example, a bottom face having a very small size of around 1.0 mm×1.5 mm. In the case of an image pickup device having only a small area to be held, provision of a group of anti-slip grooves in an anvil alone may be insufficient to ensure bonding reliability.

However, as long as the surface roughness is equal to or exceeds the lower limit of the aforementioned range, a significant anti-slip effect is exerted and reliability of bonding between the image pickup devices 20 and the wiring boards 30 is high, and as long as the surface roughness is equal to or below the upper limit of the aforementioned range, no crack may occur in the image pickup devices 20.

Figure 12A:
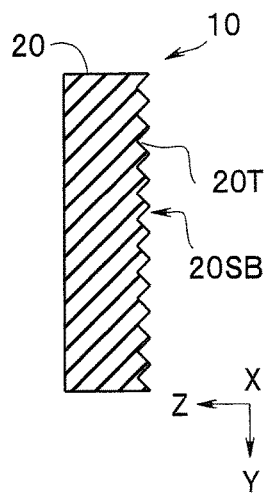
FIG. 12A is a side view of the image pickup device of the image pickup apparatus according to the embodiment.
Figure 12B:
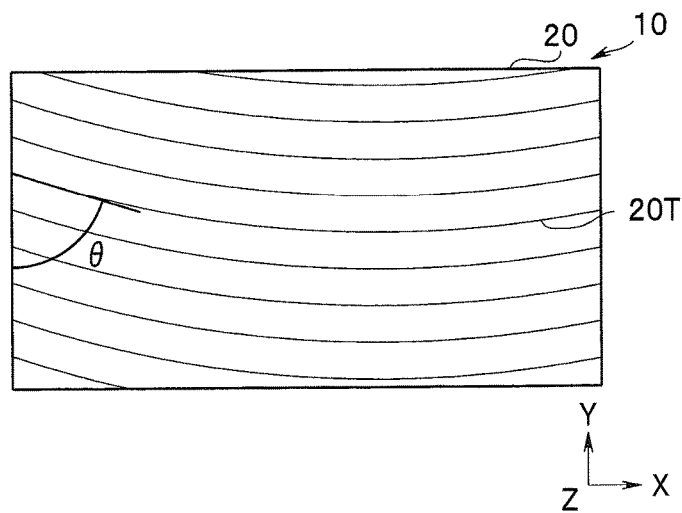
FIG. 12B is a diagram illustrating a direction of saw marks in the image pickup device according to the embodiment.

As illustrated in FIGS. 12A and 12B, in each of the plurality of image pickup devices 20 simultaneously subjected to grinding, a plurality of grooves 20T inclined so as to be substantially orthogonal to a short axis direction.

Also, if the surface roughness is within the aforementioned range and an inclination angle θ of the plurality of grooves 20T relative to the direction of the row of the bumps 23 is an angle that exceeds 45 degrees and is less than 135 degrees, a particular anti-slip effect is exerted. The inclination angle θ is preferably no less than 60 degrees and no more than 120 degrees, more preferably no less than 80 degrees and no more than 100 degrees. Here, although, to be exact, the grooves 20T, which are saw marks, are curved lines, in each image pickup device 20, the inclination angle θ is within the aforementioned range in the entire back face 20SB.

Figure 13:
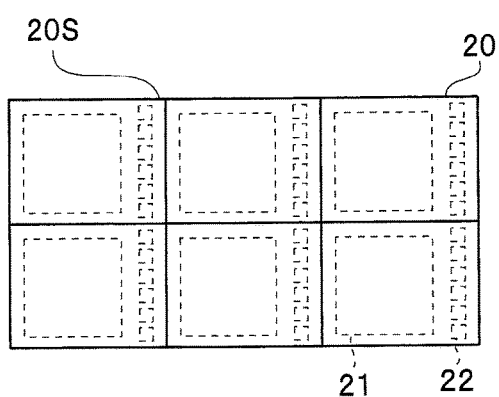
FIG. 13 is a top view of a workpiece to be ground, for the image pickup apparatus according to the embodiment.

Also, the case where grinding is performed after cutting of the silicon wafer into the individual image pickup devices 20 has been described as an example. However, as illustrated in FIG. 13, it is possible that the silicon wafer is cut into workpieces 20S each including a plurality of image pickup devices 20 and the workpieces 20S are subjected to grinding and subsequently each cut into the individual image pickup devices 20.

The workpieces 20CS are arranged on the holder 81 so that a direction of a plurality of grooves 20T (saw marks) formed in the back face 20SB of each image pickup device 20 included in each workpiece 20CS becomes a predetermined direction, that is, a direction inclined relative to the short axis direction.

After the back face grinding, each of the workpieces 20CS is cut into individual image pickup devices 20. In the case of grinding of the workpieces 20CS, arrangement of the workpieces 20CS on the holder 81 is easy.

<Step S14: Wiring Board Production>

Separately, a wiring board 30 is produced. The wiring board 30 includes, for example, an insulating resin such as polyimide as a base, and conductor wirings, for example, copper wirings. Then, copper wirings protruding from distal ends as a result of selective removal of the insulating resin of the end portions serve as flying leads 31.

A disposition pitch of the flying leads 31 and a disposition pitch of the external electrodes 22 (bumps 23) of an image pickup device 20 are set to be equal to each other.

<Step S15: Ultrasonic Bonding>

Figure 14:
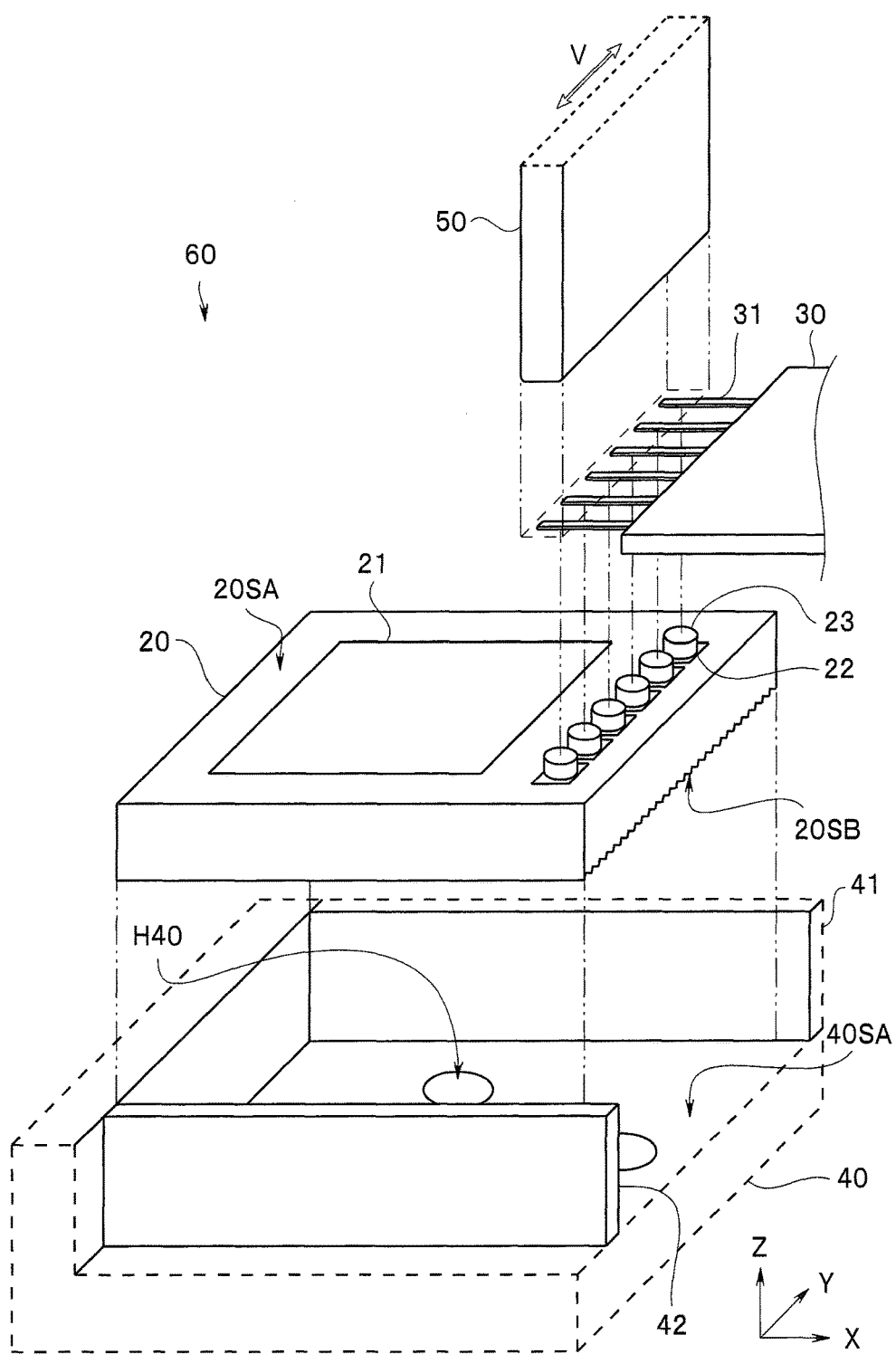
FIG. 14 is a perspective view for describing the method for manufacturing the image pickup apparatus according to the embodiment.

As illustrated in FIG. 14, an ultrasonic bonding apparatus 60 includes an anvil (anvil) 40, which is a securing stage, and an indentation tool (horn) 50 configured to ultrasonically vibrate. The indentation tool 50 is mechanically coupled to an ultrasonic transducer (not illustrated), and vibrates, for example, in a V direction at 40 kHz with a vibration amplitude of 2 µm.

In order to define and hold a position of the image pickup device 20, side clamps 41, 42 configured to secure opposite side faces of the image pickup device 20 are disposed on the anvil 40. Also, in a surface (mounting surface) 40SA, on which the image pickup device 20 is to be mounted, of the surface anvil 40, a hole H40 for vacuuming and securing a back face 20SB of the image pickup device 20 is formed. Note that the side clamps and the vacuum hole are not essential components of the anvil 40. The anvil 40 is formed of, e.g., a metal, ceramic or a resin.

The image pickup device 20 is mounted on the anvil 40. Distal end portions of the plurality of flying leads 31 of the wiring board 30 are arranged immediately above the plurality of external electrodes 22 (bumps 23) of the image pickup device 20, and ultrasonic vibration is simultaneously applied to the distal end portions while the distal end portions are pressed by the indentation tool 50.

An oxide coating and dirt at an interface between the flying leads 31 and the bumps 23 are removed by the ultrasonic vibration, and crystal grains thus come close to one another until a distance between the respective crystal grains becomes an interatomic distance, and as a result, a strong attraction force is exerted and metallurgical coupling thus occurs. At this time, the bumps 23 are crushed along an ultrasonic vibration application direction (Y direction), and streaks (ultrasonic vibration marks) are formed in the ultrasonic vibration application direction in the distal end portions of the flying leads 31, which are in contact with the indentation tool 50.

As already described, in the case of an ultracompact image pickup device, securing of the image pickup device using side clamps 41, 42 and vacuuming alone causes the image pickup device to slip upon application of ultrasonic vibration, and thus may be unable to make it easy to ensure bonding reliability.

On the other hand, grooves (saw marks) 20T formed in the back face 20SB of the image pickup device 20 have an anti-slip effect, enabling provision of high bonding reliability.

As long as the grooves 20T are inclined relative to the ultrasonic vibration application direction, that is, the grooves 20T are not parallel to the ultrasonic vibration application direction, the grooves 20T exert an anti-slip effect. In order to exert a high anti-slip effect, as already described, the grooves 20T are inclined relative to the ultrasonic vibration application direction, but an angle of the inclination is preferably an angle exceeding 45 degrees, particularly preferably an angle that is substantially orthogonal to the ultrasonic vibration application direction, that is, no less than 80 degrees.

Note that the grooves 20T are not limited to saw marks formed as a result of grinding for thickness reduction. For example, if an anti-slip effect of saw marks formed as a result of grinding is insufficient, grooves made to a predetermined specification for exerting an anti-slip effect may be formed by means of, e.g., grinding or etching.

Here, the grooves 20T exert a significant effect particularly where an ultracompact image pickup device having a bottom area of no more than 4 mm$^2$ is ultrasonically bonded to a wiring board. Although no specific lower limit of the bottom area of the image pickup device is provided, a lower limit of the bottom area is, for example, no less than 0.25 mm$^2$ because of a technical limit in handling.

Also, in the image pickup apparatus 10, the ultrasonic vibration application direction is parallel to the direction of the row of the external electrodes 22 (Y direction). Thus, the grooves 20T are formed so as to be parallel to an X direction orthogonal to the Y direction. On the other hand, it should be understood that, for example, if the ultrasonic vibration application direction is the X direction orthogonal to the direction of the row of the external electrodes 22 (Y direction), the grooves 20T are formed so as to be parallel to the Y direction orthogonal to the X direction.

Modifications of Embodiment

Next, image pickup apparatuses 10A to 10I according to modifications of the embodiment and methods for manufacturing the image pickup apparatuses 10A to 10I will be described. The image pickup apparatuses 10A to 10I, etc., in the modifications are similar to the image pickup apparatus 10, etc., in the embodiment and have functions that are the same as functions of the image pickup apparatus 10, etc., and thus, components that are the same as components of the image pickup apparatus 10, etc., are provided with reference numerals that are the same as reference numerals in the image pickup apparatus 10, etc., and description of such components will be omitted.

For an image pickup apparatus 10A according to modification 1, an image pickup device 20A is subjected to thickness reduction using a through-feed (creep feed)-type machine as a grinding machine.

Figure 15:
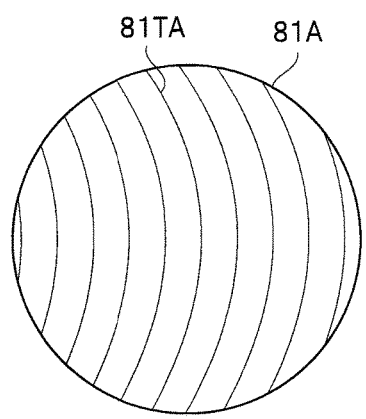
FIG. 15 is a diagram for describing a direction of saw marks in a method for manufacturing an image pickup apparatus according to modification 1 of the embodiment.

In the through-feed-type machine, saw marks 80TA in the direction illustrated in FIG. 15 are formed in image pickup devices mounted on a holder 81A.

Figure 16:
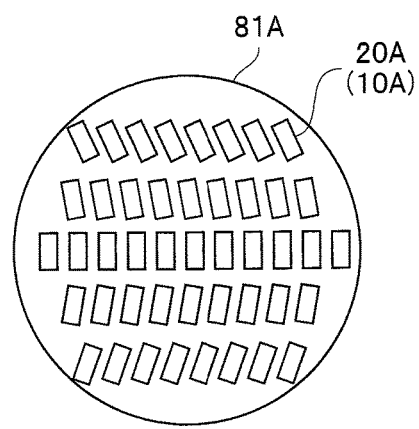
FIG. 16 is a diagram for describing arrangement of workpieces to be ground in a method for manufacturing the image pickup apparatus according to modification 1 of the embodiment.

Thus, as illustrated in FIG. 16, a plurality of image pickup devices 20A are re-arranged on the holder 81A so that saw marks are formed in the predetermined same direction.

The direction of the grooves in the image pickup device 20A of the image pickup apparatus 10A is substantially orthogonal to a short axis direction (ultrasonic vibration application direction), enabling provision of high bonding reliability.

In other words, for the grinding method, centerless in-feed grinding is preferable from the perspective of productivity. However, the present invention is not limited to cases where an in-feed machine is used, e.g., a through-feed machine may be used as long as grinding can be performed in such a manner that a direction of saw marks is made to be substantially orthogonal to a short axis direction by re-arrangement of image pickup devices.

Modification 2

Figure 17:
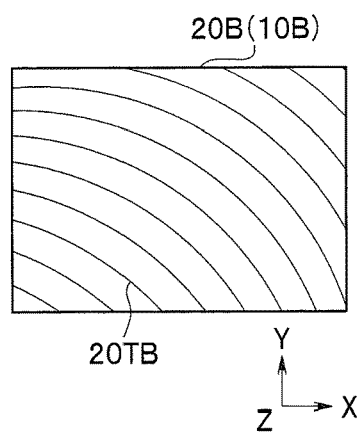
FIG. 17 is a diagram illustrating a direction of saw marks in an image pickup device according to modification 2 of the embodiment.

In an image pickup device 20B of an image pickup apparatus 10B according to modification 2, which is illustrated in FIG. 17, saw marks 20TB are inclined relative to an ultrasonic vibration application direction (Y direction). Then, an inclination angle θ exceeds 45 degrees in an entire back face 20SB.

The grooves 20TB exert an anti-slip effect, enabling the image pickup apparatus 10B to have high bonding reliability.

Modification 3

Figure 18:
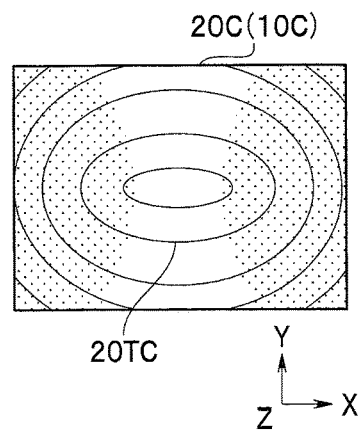
FIG. 18 is a diagram illustrating a direction of saw marks in an image pickup device according to modification 3 of the embodiment.

In an image pickup device 20C of an image pickup apparatus 10C according to modification 3, which is illustrated in FIG. 18, saw marks 20TC each have a substantially-elliptical shape. Thus, the saw marks 20TC include regions in which an angle of inclination of each saw mark 20TC relative to an ultrasonic vibration application direction (Y direction) is no more than 45 degrees. However, the saw marks 20TC also include regions (regions indicated by hatching) in which the saw marks 20TC are inclined at an angle exceeding 45 degrees relative to the ultrasonic vibration application direction (Y direction), and thus exert an anti-slip effect.

Modifications 4, 5

Figure 19:
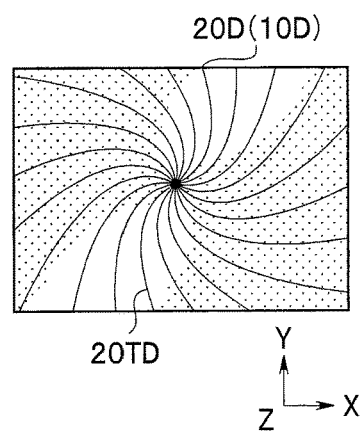
FIG. 19 is a diagram illustrating a direction of saw marks in an image pickup device according to modification 4 of the embodiment.

In an image pickup device 20D of an image pickup apparatus 10D according to modification 4, which is illustrated in FIG. 19, circular arc saw marks 20TD extend radially from a center.

Figure 20:
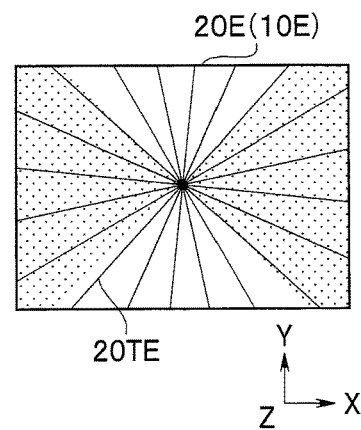
FIG. 20 is a diagram illustrating a direction of saw marks in an image pickup device according to modification 5 of the embodiment.

In an image pickup device 20E of an image pickup apparatus 10E according to modification 5, which is illustrated in FIG. 20, linear saw marks 20TE extend radially from a center.

The saw marks 20TD, 20TE each include regions in which an angle of inclination of each saw mark 20TD, 20TE relative to an ultrasonic vibration application direction (Y direction) is no more than 45 degrees. However, the saw marks 20TD, 20TE also include regions (regions indicated by hatching) in which the saw marks 20TD, 20TE are inclined at an angle exceeding 45 degrees relative to the ultrasonic vibration application direction (Y direction), and thus exert an anti-slip effect.

Modification 6

Figure 21:
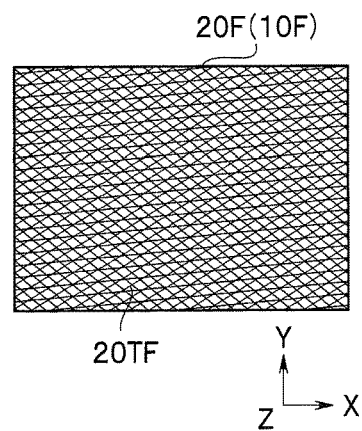
FIG. 21 is a diagram illustrating a direction of saw marks in an image pickup device according to modification 6 of the embodiment.

In an image pickup device 20F of an image pickup apparatus 10F according to modification 6, which is illustrated in FIG. 21, saw marks 20TF are substantially linear, but each saw mark 20TF is random.

The saw marks 20TF include parts in which an angle of inclination of each saw mark 20TF relative to an ultrasonic vibration application direction (Y direction) is no more than 45 degrees. However, the saw marks 20TF also include parts in which the saw marks 20TF are inclined at an angle exceeding 45 degrees relative to the ultrasonic vibration application direction (Y direction), and thus exert an anti-slip effect.

Modification 7

Figure 22:
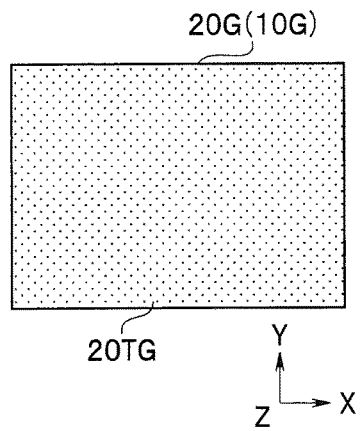
FIG. 22 is a diagram illustrating a direction of saw marks in an image pickup device according to modification 7 of the embodiment.

In an image pickup device 20G of an image pickup apparatus 10G according to modification 7, which is illustrated in FIG. 22, a back face 20SB includes a random fine projection/recess pattern 20TG. The projection/recess pattern 20TG includes, for example, etching marks, which can be regarded as fine grooves.

Microscopically, the pattern 20TG includes parts in which the pattern 20TG is inclined at an angle of no more than 45 degrees relative to an ultrasonic vibration application direction (Y direction). However, the pattern 20TG also includes parts in which the pattern 20TG is inclined at an angle exceeding 45 degrees relative to the ultrasonic vibration application direction (Y direction) and thus exerts an anti-slip effect.

As described above, the image pickup devices of the image pickup apparatuses according to modifications 2 to 7 each exert an anti-slip effect if a part of the back face 20SB includes a region in which saw marks are inclined at an angle exceeding 45 degrees relative to the ultrasonic vibration application direction (Y direction). In particular, forming saw marks inclined at an angle exceeding 45 degrees in a region having an area that makes up no less than 25% of the area of the back face 20SB is particularly preferable to exert an anti-slip effect.

Modification 8

Figure 23:
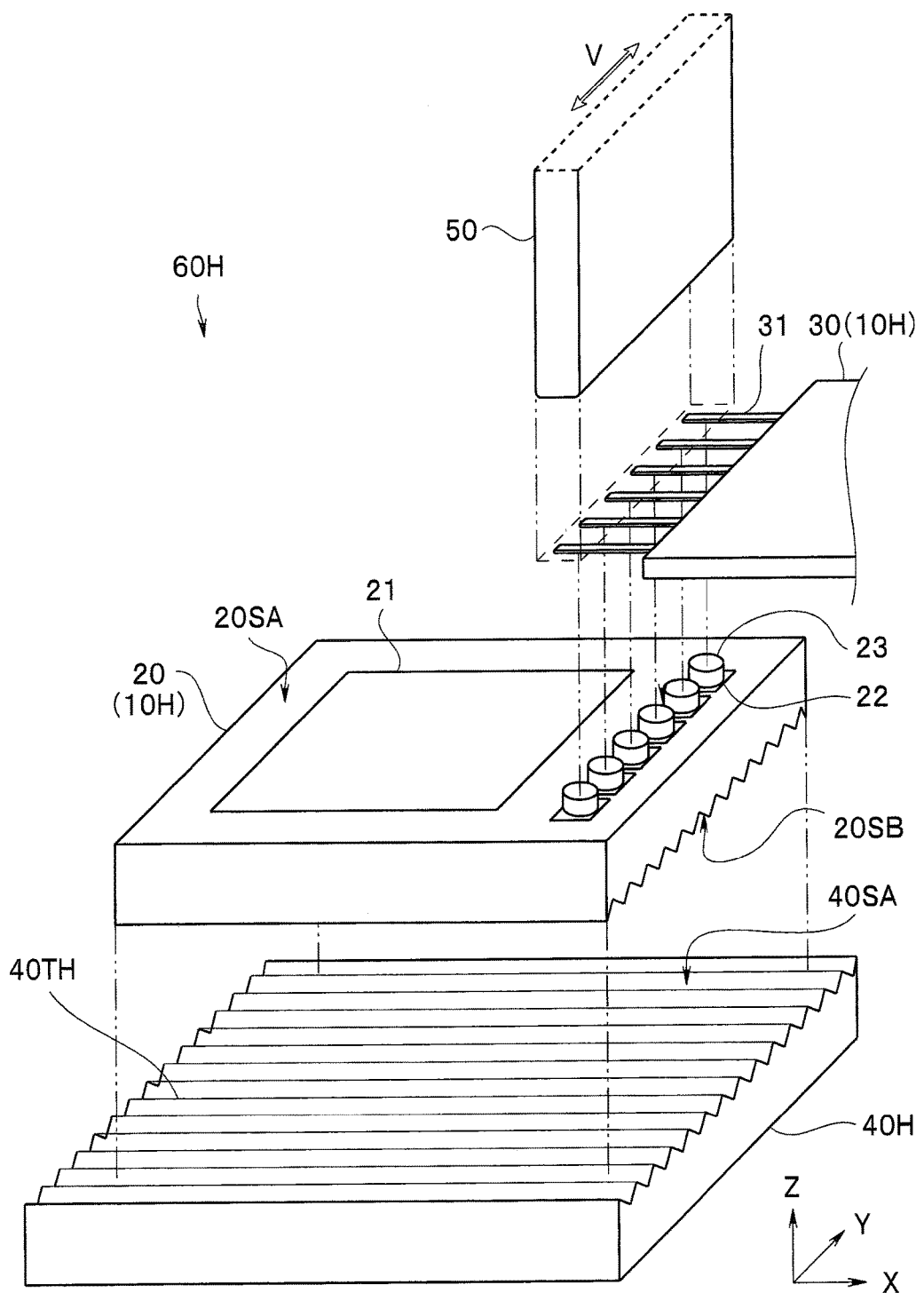
FIG. 23 is a perspective view for describing a method for manufacturing an image pickup apparatus according to modification 8 of the embodiment.

In an ultrasonic bonding apparatus 60H used in a method for manufacturing an image pickup apparatus 10H according to modification 8, which is illustrated in FIG. 23, an anvil 40H is different from the anvil of the ultrasonic bonding apparatus 60 in the embodiment.

In a surface 40SA of the anvil 40H, a plurality of grooves 40TH in a direction orthogonal to an ultrasonic vibration direction are formed. Then, a surface roughness Rz40 of the surface 40SA is, for example, no less than 0.5 μm and no more than 10 μm and thus is substantially the same as a surface roughness Rz20 of a back face 20SB of an image pickup device 20.

Thus, when ultrasonic vibration is applied, projections and recesses of groove 20TH and projections and recesses of the grooves 40TH are fitted together, and thus, a particularly-high anti-slip effect is exerted.

Note that the surface roughness Rz20 of the grooves 20TH and the surface roughness Rz40 of the grooves 40TH being substantially the same, for example, a difference between the surface roughness Rz20 and the surface roughness Rz40 being ±20%, is particularly preferable for fitting the grooves 20TH and the grooves 40TH together, a predetermined effect can be obtained if the difference is no more than ±50%. For example, if the surface roughness Rz20 of the image pickup device 20 is 2 μm, it is preferable that the surface roughness Rz40 of the anvil 40H be no less than 1 μm and no more than 4 μm.

Modification 9

Figure 24:
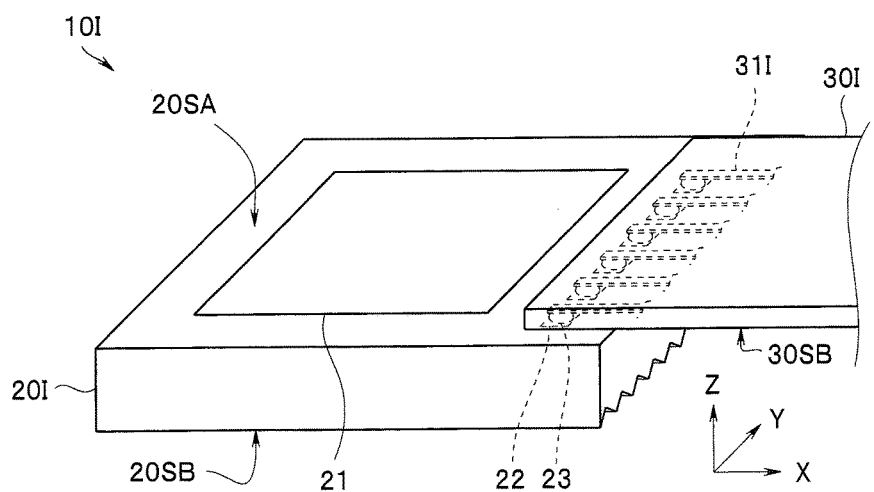
FIG. 24 is a perspective view for describing an image pickup apparatus according to modification 9 of the embodiment.

In an image pickup device 20I of an image pickup apparatus 10I according to modification 9, which is illustrated in FIG. 24, end portion electrodes 31I of a wiring board 30I are electrode pads disposed on a back face 30SB.

In other words, the end portion electrodes 31I of the wiring board 30I are not limited to flying leads.

Also, the bumps may be disposed not on the external electrodes 22 of the image pickup device but on the end portion electrodes of the wiring board. Furthermore, instead of the bumps, the end portion electrodes of the wiring board may each include a protrusion portion.

Also, although the above embodiment has been described in terms of a case where the endoscope is a medical endoscope, it should be understood that the present invention is not limited to this case and is applicable also to a small-diameter industrial endoscope.

The present invention is not limited to the above-described embodiment and the like, and various modifications, alterations and the like are possible without departing from the spirit of the present invention.

What is claimed is:
1. An image pickup apparatus for an endoscope, the image pickup apparatus comprising:

an image pickup device including a row of external electrodes provided on an end portion of an image sensor; and a wiring board including end portion electrodes ultrasonically bonded to the external electrodes, wherein a plurality of grooves are formed in a back face of the image pickup device, the back face opposing a surface on which the image sensor is disposed, and the plurality of grooves are inclined relative to a vibration direction of ultrasonic vibration during ultrasonic bonding.

2. The image pickup apparatus for an endoscope according to claim 1, wherein the vibration direction is a direction of the row of the external electrodes.

3. The image pickup apparatus for an endoscope according to claim 2, wherein the plurality of grooves are saw marks resulting from grinding.

4. The image pickup apparatus for an endoscope according to claim 3, wherein the plurality of grooves are inclined at an angle exceeding 45 degrees relative to the vibration direction.

5. The image pickup apparatus for an endoscope according to claim 4, wherein a surface roughness Rz, in a direction orthogonal to the vibration direction, of the back surface of the image pickup sensor is no less than 0.5 μm and no more than 10 μm.

6. An image pickup apparatus for an endoscope, the image pickup apparatus comprising:

an image pickup device including a row of external electrodes provided on an end portion of an image sensor, the image pickup device having a bottom area of no less than 0.25 mm$^2$ and no more than 4 mm$^2$; and a wiring board including end portion electrodes ultrasonically bonded to the external electrodes, wherein a saw mark is formed by grinding in a back face of the image pickup device, the back face opposing a surface on which the image sensor is disposed, the saw mark is inclined at an angle of no less than 80 degrees and no more than 100 degrees relative to a direction of the row of the external electrodes in the entire back face, and a surface roughness Rz, in a direction orthogonal to the direction of the row of the external electrodes, of the back face is no less than 0.5 μm and no more than 10 μm.

7. A method for manufacturing an image pickup apparatus for an endoscope, the image pickup apparatus including an image pickup device including a row of external electrodes provided on an end portion of an image sensor, and a wiring board including end portion electrodes ultrasonically bonded to the respective external electrodes, the method comprising:

forming a plurality of image sensors on a first principal surface of a semiconductor substrate;

cutting the semiconductor substrate to produce a plurality of image pickup devices;

re-arranging the plurality of image pickup devices in a grinding machine in such a manner that a direction of saw marks to be formed is inclined relative to a short axis direction of the image pickup device;

grinding back faces of the plurality of image pickup devices, the back faces opposing the respective surfaces upon which the image sensors are disposed, to form saw marks inclined relative to a vibration direction of ultrasonic vibration during ultrasonic bonding; and ultrasonically bonding the external electrodes of the image pickup devices, mounted on an anvil of an ultrasonic bonding apparatus, and the end portion electrodes of the wiring board to each other.

8. The method for manufacturing an image pickup apparatus for an endoscope according to claim 7, wherein:

a plurality of grooves are formed in a surface of the anvil; and a surface roughness of the surface of the anvil and a surface roughness of the back face of the image pickup device are same.

\* \* \* \* \*